US009615998B2

(12) United States Patent
Rabih

(10) Patent No.: US 9,615,998 B2
(45) Date of Patent: Apr. 11, 2017

(54) FILLING APPARATUS FOR DRUG CONTAINERS AND METHOD FOR FILLING THE SAME

(71) Applicant: Jamaleddine Rabih, Pierrefond (CA)

(72) Inventor: Jamaleddine Rabih, Pierrefond (CA)

( * ) Notice: Subject to any disclaimer, the term of this patent is extended or adjusted under 35 U.S.C. 154(b) by 236 days.

(21) Appl. No.: 14/368,214

(22) PCT Filed: Dec. 21, 2012

(86) PCT No.: PCT/CA2012/001194
§ 371 (c)(1),
(2) Date: Jun. 23, 2014

(87) PCT Pub. No.: WO2013/091087
PCT Pub. Date: Jun. 27, 2013

(65) Prior Publication Data
US 2015/0000784 A1    Jan. 1, 2015

Related U.S. Application Data

(60) Provisional application No. 61/579,825, filed on Dec. 23, 2011.

(51) Int. Cl.
| | | |
|---|---|---|
| A61J 1/20 | (2006.01) |
| A61M 5/178 | (2006.01) |
| B65B 31/02 | (2006.01) |
| B65B 3/00 | (2006.01) |
| A61J 1/22 | (2006.01) |

(52) U.S. Cl.
CPC ............... *A61J 1/2096* (2013.01); *A61J 1/20* (2013.01); *A61J 1/22* (2013.01); *A61M 5/1782* (2013.01); *B65B 3/003* (2013.01); *B65B 31/02* (2013.01)

(58) Field of Classification Search
CPC ... A61J 1/20; A61J 1/2096; A61J 1/22; B65B 3/003; B65B 31/02; A61M 5/1782
USPC ..................................... 141/2, 18, 21, 25–27
See application file for complete search history.

(56) References Cited

U.S. PATENT DOCUMENTS

| | | | | |
|---|---|---|---|---|
| 3,935,883 A * | 2/1976 | Stach | ...................... | B65B 3/003 |
| | | | | 141/27 |
| 5,911,252 A * | 6/1999 | Cassel | ..................... | B65B 3/003 |
| | | | | 141/234 |
| 6,805,170 B2 * | 10/2004 | Py | .............................. | A61J 1/18 |
| | | | | 141/2 |
| 7,128,105 B2 * | 10/2006 | Tribble | ..................... | A61J 1/20 |
| | | | | 141/198 |
| 7,163,031 B2 * | 1/2007 | Graves | .................... | G21F 5/015 |
| | | | | 141/104 |

(Continued)

*Primary Examiner* — Nicolas A Arnett
(74) *Attorney, Agent, or Firm* — Brouillette Legal Inc.; Damien Calvet

(57) ABSTRACT

An apparatus for filling drug containers such as syringes, and related filling methods, are disclosed. The apparatus uses a removable pumping syringe mounted to the apparatus and located intermediate between the bulk source of drug and the container (e.g. syringe) to be filled such that the drug is first pumped into the pumping syringe and then pumped into the container (e.g. syringe). Actuation of the intermediate pumping syringe is effected with a linear actuator such as a step motor which is engaged to the plunger of the pumping syringe. The linear actuator is controlled by a controller which typically allows different filling and calibrating procedures.

30 Claims, 5 Drawing Sheets

(56) References Cited

U.S. PATENT DOCUMENTS

| | | | | |
|---|---|---|---|---|
| 7,343,943 B2* | 3/2008 | Khan | ................ | B65B 3/003 |
| | | | | 141/2 |
| 7,703,483 B2* | 4/2010 | Hartman | ............. | B65B 3/003 |
| | | | | 141/27 |
| 7,712,491 B2* | 5/2010 | Tochon-Danguy | ..... | G21F 5/015 |
| | | | | 141/105 |
| 8,069,886 B1* | 12/2011 | Yanke | ............. | A61J 1/20 |
| | | | | 141/252 |
| 8,220,504 B2* | 7/2012 | Hartman | ............. | B65B 3/003 |
| | | | | 141/27 |
| 8,807,177 B2* | 8/2014 | Strangis | ............ | B63C 9/0005 |
| | | | | 141/104 |
| 2004/0256026 A1* | 12/2004 | Py | ............. | B29C 66/7394 |
| | | | | 141/329 |
| 2012/0029428 A1* | 2/2012 | Neer | ............. | A61M 5/007 |
| | | | | 604/131 |
| 2014/0027009 A1* | 1/2014 | Riley | ............. | A61M 5/007 |
| | | | | 141/2 |
| 2014/0157731 A1* | 6/2014 | Perazzo | ........... | B65B 57/02 |
| | | | | 53/473 |
| 2015/0251781 A1* | 9/2015 | Matsukuma | .......... | A61J 1/20 |
| | | | | 141/2 |

* cited by examiner

FILLING APPARATUS FOR DRUG CONTAINERS AND METHOD FOR FILLING THE SAME

CROSS-REFERENCE TO RELATED APPLICATIONS

The present patent application claims the benefits of priority of U.S. Provisional Patent Application No. 61/579,825, entitled "Filling Apparatus for Drug Containers and Method for Filling the Same", and filed at the United States Patent and Trademark Office on Dec. 23, 2011, the content of which is incorporated herein by reference.

FIELD OF THE INVENTION

The present invention generally relates to apparatuses, systems and/or methods for filling liquid solutions or liquid drugs in different containers, and more particularly relates to apparatuses, systems and/or methods for filling liquid solutions or liquid drugs into syringes and/or other medical containers.

BACKGROUND OF THE INVENTION

Medical doctors regularly prescribe drugs to be taken by injection or in oral format, whether it is to be taken in a hospital or outside of the hospital. The preparation of these prescriptions by pharmacists often includes the filling, or pre-filling, of containers to contain these drugs. Such containers may include syringes, cassettes, bags, vials, etc. It is thus often critical for pharmacists to ensure that the filling of the containers be performed with great accuracy. It is also important that the filling of the containers be performed safely and with minimal risk of contamination.

The process of filling syringes has revealed a number of technical problems. Due to the physical manufacturing imperfections of the syringe cylinder as well as the friction of the plunger's seal, significant variations in back pressure result during the filling process. These variations can affect and vary the total volume transferred to the syringe.

Health and safety regulations also prohibit any volumetric discrepancies of more than 10% for any oral drugs substance and only 2% for narcotic substances. In that several syringes are typically filled with a given dose of drug, it is critical that the transfer of liquid be performed rapidly and with high accuracy.

Traditionally, and still recently, peristaltic pumps have been employed in medical applications for their unique ability to force liquid through tubes without direct contact. Non-limitative examples of filling apparatuses using peristaltic pumps are shown in U.S. Pat. Nos. 3,662,517; 6,976,349 and 7,703,483.

However, with increased back pressure, the flexible tubing can lead to both errors in accuracy as well as substantial residual pressure causing spillage as the filled syringes are removed.

One way to overcome the problem of back pressure is to use an intermediate pumping syringe between the bulk source of drug and the receiving syringe to be filled.

This solution has been proposed in U.S. Pat. Nos. 3,935,883; 4,187,890 and 5,911,252.

However, the apparatuses disclosed in U.S. Pat. Nos. 3,935,883 and 4,187,890 use a motor-driven mechanical crank to actuate the plunger of the pumping syringe. Such a mechanical assembly does not provide the level of accuracy required by health and safety regulations. Moreover, these apparatuses do not provide for calibration.

U.S. Pat. No. 5,911,252 does propose a more advanced apparatus. But again, the precise actuation of the plunger of the pumping syringe is not addressed and the level of accuracy required by health and safety regulations is likely not complied with.

Hence, there is a need for a novel apparatus for filling syringes and other drug containers, as well as novel methods relating thereto, which mitigates at least some shortcomings of the prior art.

SUMMARY OF THE INVENTION

A filling apparatus in accordance with the principles of the present invention generally mitigates at least some of the shortcomings of prior filling apparatuses by controlling the intermediate pumping syringe with a linear actuator.

Hence, a filling apparatus in accordance with the principles of the present invention generally comprises an actuating member configured to releasably engage at least one plunger of at least one intermediate pumping syringe and driven by a linear actuator, typically a step motor. The apparatus also comprises a controller operatively connected to the linear actuator for controlling the displacements of the actuating member and thus of the at least one plunger of the at least one intermediate pumping syringe.

The invention is also directed to a filling apparatus for filling a container with a liquid, the apparatus comprising:
 a housing supported by a base structure, the base structure comprising a supporting structure configured to releasably support at least one barrel of at least one pumping syringe, the supporting structure comprising at least one channel formed into the housing and configured to releasably support the at least one barrel of the at least one pumping syringe;
 an actuating member slidingly mounted to the base structure, the actuating member being configured to releasably engage at least one plunger of the at least one pumping syringe;
 a linear actuator fixedly mounted to the base structure and drivingly connected to the actuating member for linearly displacing the actuating member, wherein the linear actuator comprises a step motor driving a threaded shaft drivingly engaged to the actuating member such that rotation of the threaded shaft causes the actuating member to slide; and
 a controller operatively connected to the linear actuator for controlling the linear actuator according to a pre-determined program;
 wherein the step motor, the linear actuator and the actuating member are protected by the housing and remain accessible via at least one door providing access to the at least one channel and to the actuating member such as to protect the at least one channel and the actuating member from contaminants; wherein the at least one door is operatively connected to the controller such that opening the at least one door during will cause the apparatus to stop completely.

The invention is further directed to a filling apparatus for filling a syringe with a liquid, the apparatus comprising:
 a base structure comprising a housing, the housing comprising at least one channel configured to releasably support at least one barrel of at least one pumping syringe;
 an actuating member slidingly mounted to the base structure and within the housing, the actuating member being configured to releasably engage at least one plunger of the at least one pumping syringe;

a linear actuator mounted to the base structure and within the housing, the linear actuator being drivingly connected to the actuating member for linearly displacing the actuating member, wherein the linear actuator comprises a step motor driving a threaded shaft drivingly engaged to the actuating member such that rotation of the threaded shaft causes the actuating member to slide; and a programmable controller operatively connected to the linear actuator for controlling the linear actuator according to a predetermined program;

wherein the housing comprises at least one door providing access to the at least one channel and to the actuating member such as to protect the at least one channel and the actuating member from contaminants, the at least one door being operatively connected to the programmable controller such that opening the at least one door causes the apparatus to stop completely.

To fill a container with a liquid, the intermediate pumping syringe is fluidly connected to a source of the liquid and to the container to be filled via a double check T-valve. The valve allows the liquid to flow from the source and into the intermediate pumping syringe, and then out of the intermediate pumping syringe and into the container.

In typical though non-limitative embodiments, the source of liquid is connected to the valve via flexible tubing while the container to be filled is connected to the valve via high-pressure connecting tubing.

In typical though non-limitative embodiments, the actuating member is slidingly mounted to a base structure (e.g. a base plate) while the linear actuator is fixedly mounted to the base structure. The base structure typically comprises a sliding structure to slidingly support the actuating member. In typical though non-limitative embodiments, the sliding structure comprises at least one rod, mounted between a pair of supporting walls, and to which the actuating member is slidingly mounted.

To properly support the at least one intermediate pumping syringe, the base structure may comprise a support structure configured to releasably support at least one barrel of the at least one intermediate pumping syringe.

In typical though non-limitative embodiments, the base structure comprises a housing to hide the internal components of the apparatus. In such embodiments, the support structure may comprise at least one channel formed in the housing and configured to receive the at least one barrel of the at least one intermediate pumping syringe.

The housing may also comprise a control panel in communication with the controller and allowing the user to input data into the apparatus for programming a filling program or for calibration purposes. In that sense, the control panel typically comprises a keyboard and a display screen.

In order to provide proper support for the connecting tubing and/or for the container to be filled, the apparatus may comprise at least one receiving structure mounted to the base structure and configured to support and hold the connecting tubing. In some embodiments, the connecting tubing may be terminated by a container connector to provide proper connection between the connecting tubing and the container to be filled. If the container to be filled is small enough (e.g. a syringe), the container might be mounted directly to the connector and thus supported by the receiving structure.

In use, an intermediate pumping syringe will first be installed into the apparatus such that its plunger, typically its free extremity, is engaged by the actuating member. Then, the intermediate pumping syringe will be fluidly connected to the source of liquid and to a container to be filled via the double check T-valve and the appropriate tubing. Then, the controller will initiate the filling sequence. Firstly, the controller will instruct the linear actuator to linearly actuate the actuating member such as to pull the plunger and cause a predetermined amount of liquid to flow from the source and into the intermediate pumping syringe, and secondly, the controller will instruct the linear actuator to linearly actuate the actuating member such as to push back the plunger and cause the predetermined amount of liquid to flow out of the intermediate pumping syringe and into the container.

Once the container is properly filled, it can be removed or disconnected and replaced by another container to be filled. The filling sequence can be repeated for as many containers as needed.

In typical applications, the container to be filled is a syringe.

By using a linear actuator, the filling apparatus in accordance with the principles of the present invention is more precise than prior filling apparatuses.

Other and further aspects and advantages of the present invention will be obvious upon an understanding of the illustrative embodiments about to be described or will be indicated in the appended claims, and various advantages not referred to herein will occur to one skilled in the art upon employment of the invention in practice. The features of the present invention which are believed to be novel are set forth with particularity in the appended claims.

BRIEF DESCRIPTION OF THE DRAWINGS

The above and other aspects, features and advantages of the invention will become more readily apparent from the following description, reference being made to the accompanying drawings in which.

DETAILED DESCRIPTION OF THE PREFERRED EMBODIMENT

Novel apparatus and methods for filling syringes and other drug containers will be described hereinafter. Although the invention is described in terms of specific illustrative embodiments, it is to be understood that the embodiments described herein are by way of example only and that the scope of the invention is not intended to be limited thereby.

Figure 1:
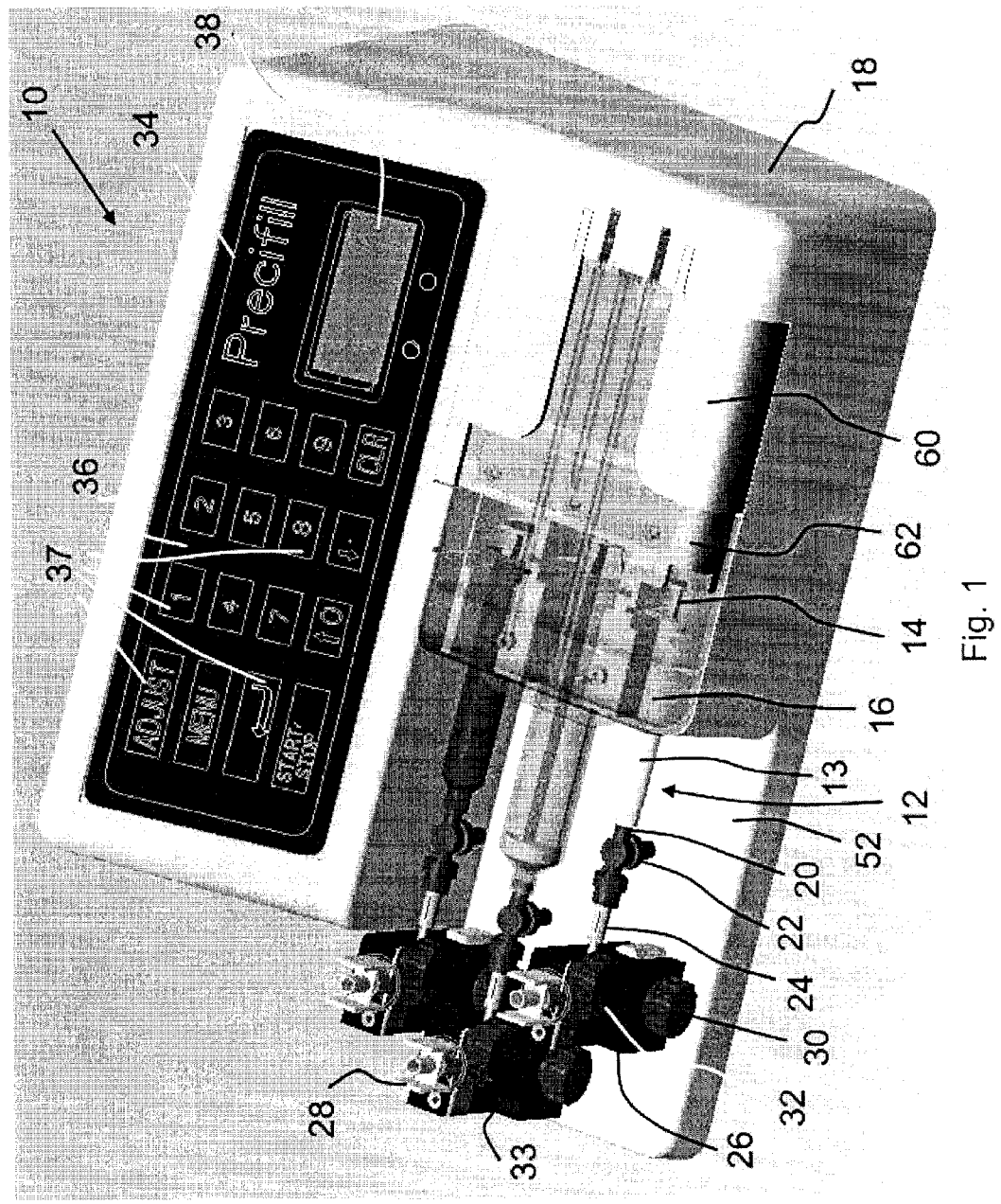
FIG. 1 is a perspective view of an embodiment of a filling apparatus in accordance with the principles of the present invention.

Broadly, an apparatus 10, in accordance with the principles of the present invention, allows the precise filling of syringes, and/or other drug containers, by precisely actuating the plunger 14 of at least one intermediate pumping syringe 12. In the apparatus of FIG. 1, three pumping syringes 12 of different capacities can be used.

In the present apparatus 10, the three pumping syringes 12 are syringes of 3 cc, 10 cc and 30 cc made by Becton, Dickinson and Co. These types of syringes are commonly used in the healthcare field.

Though the present apparatus 10 can be used with three different pumping syringes 12, only one pumping syringe 12 is used at any given time. Also, the general functioning remains the same for each pumping syringe 12 so only one pumping syringe 12 will be described hereafter. Understandably, other embodiments could be used with more or less than three different pumping syringes.

In the present embodiment, the barrel 13 of the pumping syringe 12 is mounted into a semi-cylindrical channel 16 formed in the housing 18 of the apparatus 10. As it will be explained in more details below, the plunger 14 of the pumping syringe 12 is engaged by an actuating element or member 40 releasably coupled to the plunger 14.

In order to minimize any back-pressure problems caused by flexible tubing, the Luer tip 20 of the pumping syringe 12 is directly fluidly connected to a dual check T-valve 22. Valve 22 is of the type that allows fluid in one direction at the time. The valve 22 is further fluidly connected to a bulk source of drug (not shown in FIG. 1), typically via a flexible tubing, and to the receiving syringe to be filled (not shown in FIG. 1) by a high pressure tubing 24.

To hold the receiving syringe firmly in place during the filling procedure which will be described below, the apparatus 10 comprises three adjustable syringe receiving stations 26, one for each of the three possible pumping syringes 12. As for the pumping syringes 12, only one receiving station 26 will be described hereafter. Understandably, the number of adjustable syringe receiving stations 26 generally corresponds to the number of different pumping syringes 12.

The receiving station 26 is secured to the housing 18 of the apparatus 10 and is typically aligned with its associated pumping syringe 12 as illustrated in FIG. 1. In the present embodiment, the position of each receiving station 26 on the housing 18 is predetermined to match the size of its corresponding pumping syringe 12. However, in other embodiments, the position of each receiving station 26 on the housing 18 could be adjustable.

Figure 2:
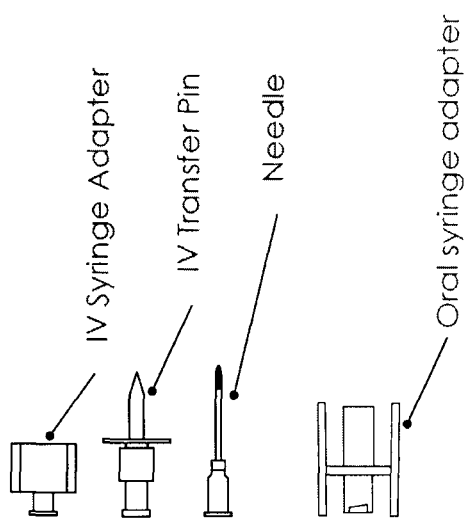
FIG. 2 is a plan view of different container connectors.

The receiving station 26 holds the high pressure tubing 24, which is connected at one end to the valve 22, and which is provided, at the other end, with a syringe connector 28. The syringe connector 28 is typically, though not necessarily, an oral syringe adapter as shown in FIG. 2. However, depending on the type of containers, other connector 28 could be used as also shown in FIG. 2. For instance, intravenous ("IV") syringe adapter, IV pin, needle, etc. A direct connection to the Luer is also possible (not shown) for different kinds of cassettes or containers. IV bags can also be filled by connecting a needle to the Luer (not shown). The syringe connector 28 is configured to fluidly engage the Luer tip of the receiving syringe during the filling procedure.

As it will be understood, the configuration of the receiving station 26 implies that the receiving syringe is in an upright position, with the tip facing down, during the filling procedure. This configuration generally avoids spillage when the filled syringe is removed from the receiving station 26. The position of other types of containers could however be different.

To adjust the position of the receiving station 26 and to allow the installation, removal and replacement of the high pressure tubing 24, the receiving station 26 comprises two knobs 30 and 32. Knobs 30 and 32 control a holding plate 33 which holds the high pressure tubing 24.

Still referring to FIG. 1, the housing 18 also comprises a control panel 34 having a keyboard 36 with several keys 37, and a display screen 38. As it will be best understood below, the control panel 34 is used during the calibrating procedure which will be described below and during the filling procedure.

Figure 3:
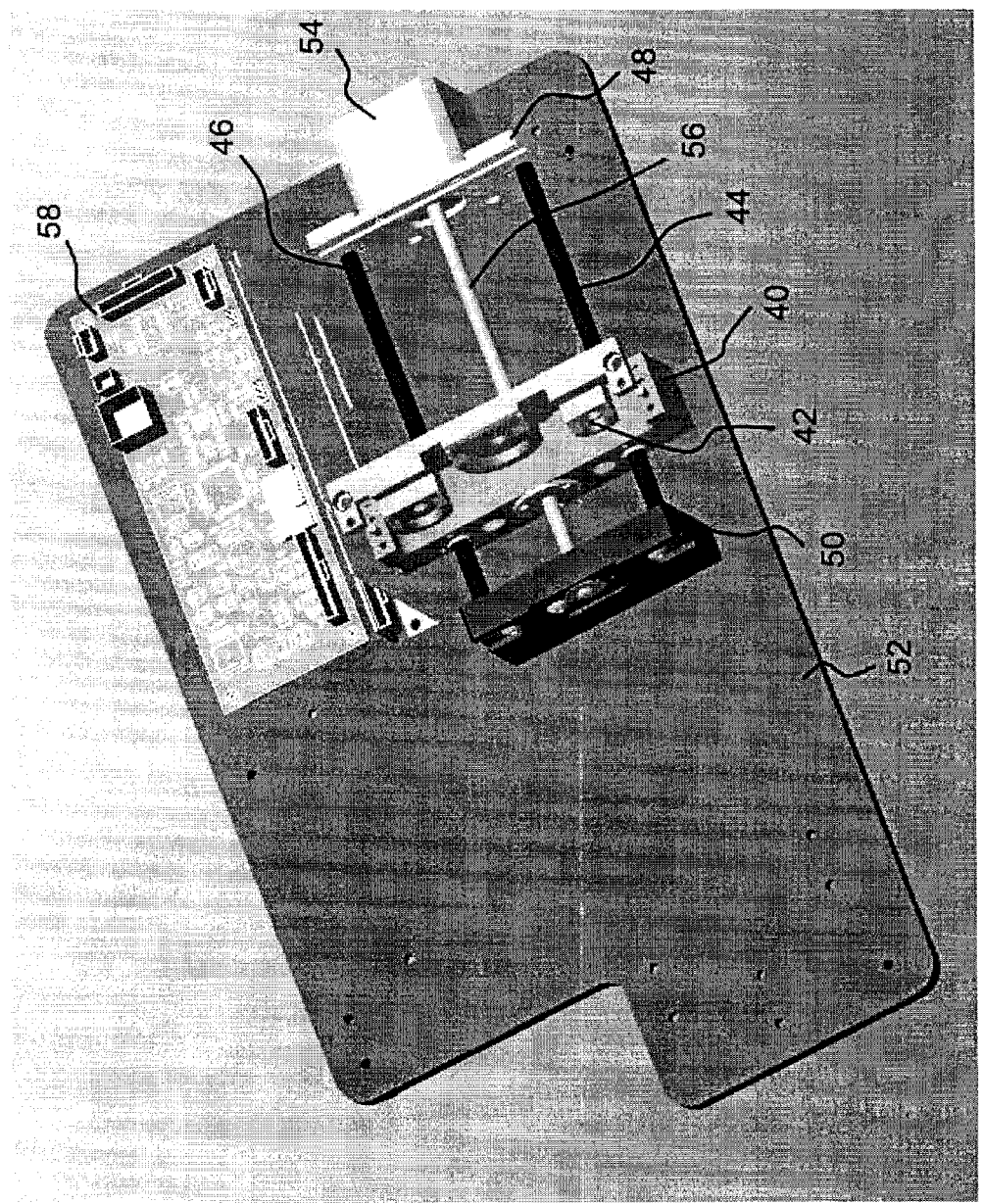
FIG. 3 is a front fragmentary perspective view of the filling apparatus of FIG. 1.
Figure 4:
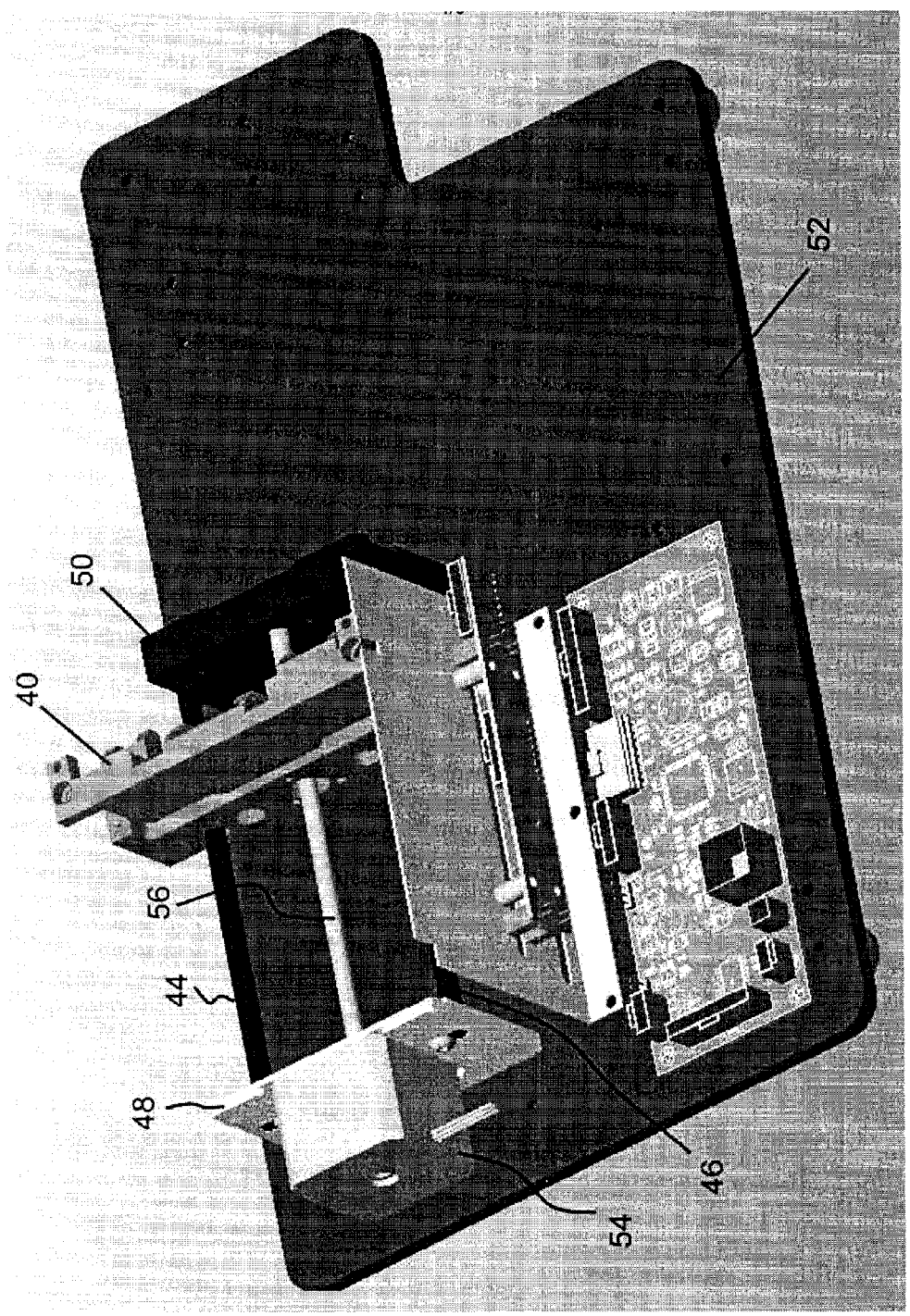
FIG. 4 is a rear fragmentary perspective view of the filling apparatus of FIG. 1.

Referring now to FIGS. 3 and 4, the inner workings of the motorized actuator of the plunger 14 are shown in greater details. For the sake of clarity, the housing 18 of the apparatus 10 is removed.

As already mentioned above, the plunger 14 of the pumping syringe 12 is engaged by the actuating member 40. In that sense, the wall element 40 comprises three semi-circular plunger engaging grooves 42, one for each of the three pumping syringes 12, which are suitably shaped and sized to snugly receive the flat and circular thumb rest of the plunger 14.

The wall element 40 is mounted for sliding movement on two typically cylindrical rods 44 and 46 extending between supporting walls 48 and 50. Understandably, supporting walls 48 and 50 are fixedly mounted to the base 52 of the apparatus 10.

Supporting wall 48 further supports a step motor 54 which drives a threaded shaft 56 mounted at its other end to the supporting wall 50. The threaded shaft 56 is drivingly engaged to the actuating member 40, via appropriate meshing elements (not shown), such that rotation of the threaded shaft 56 causes the actuating member 40 to slide along the two rods 44 and 46. Understandably, the maximum distance traveled by the wall element 40 is limited to the size of the pumping syringe 12 used.

In the present apparatus 10, the step motor 54 is a Haydon™ 4300 Series Size 17 hybrid linear actuator. Though other step motors could be used, the Haydon™ 4300 Series Size 17 hybrid linear actuator has been found to give precise and repeatable results. In that sense, it is to be noted that the step motor 54 used in the present embodiment can rotate by increment of 1.8°, which corresponds to a linear displacement of 0.024834 mm, thereby providing precise linear actuation of the plunger 14.

As shown in FIGS. 3 and 4, the step motor 54 is controlled by a controller 58, embodied, in the present apparatus 10, as a circuit board, which comprises a microcontroller, memories and other associated components.

Understandably, the controller 58 is in communication with the control panel 34 and thus with the keyboard 36 and the display screen 38.

Returning to FIG. 1, it will be understood that the step motor 54, the threaded shaft 56 and the actuating member 40 are protected by the housing 18 though they remain accessible via two overlapping doors 60 and 62.

Door 62 overlaps door 60, and generally covers the upper half portion of the pumping syringe 12, including the plunger 14, such that accidents (e.g. injured fingers) are prevented and that the plunger 14 remains relatively protected from contaminants. Door 62 is hingedly mounted to the housing 18.

Door 60 is located under door 62 and generally covers the threaded shaft 56 and the step motor 54. Door 60 is also hingedly mounted to the housing 18. However, to open door 60, it is necessary to open door 62 first since door 62 overlaps door 60 as shown in FIG. 1.

In the present apparatus 10, both doors 60 and 62 are connected to the controller 58, typically via a switch (not shown) such that opening of any of the doors during either a calibrating procedure or a filling procedure will cause the apparatus 10 to stop completely. Doors 60 and 62 therefore provide a certain level of safety and protection to the operator.

In operation, when a new batch of syringes (or other containers) needs to be filled with a predetermined amount of liquid drugs (or other substances), a new pumping syringe 12 is installed into the appropriate channel 16 and the thumb rest of its plunger 14 is inserted into the groove 42 of the actuating member 40. The new pumping syringe 12 is also connected to a new dual check valve 22 which is itself connected to a new high pressure tubing 24. To install the high pressure tubing 24 in the proper receiving station 26, the operator actuates knob 32. The valve 22 is also fluidly connected to the drug bulk source via new flexible tubing.

It is important that new material (i.e. pumping syringe 12, check valve 22, tubing 24 and connector 28) be used for each new batch of syringe filling in order to avoid contamination and to obtain proper calibration.

Notably, if the drug in the drug bulk source is a suspension, the drug may settle at the bottom of the bulk source container. It is thus necessary to mix or refill the container at appropriate frequency to ensure that the proper concentration of drug is in suspension for all doses of drug packaged. It is also possible to use a stirrer during the filling procedure.

Figure 5:
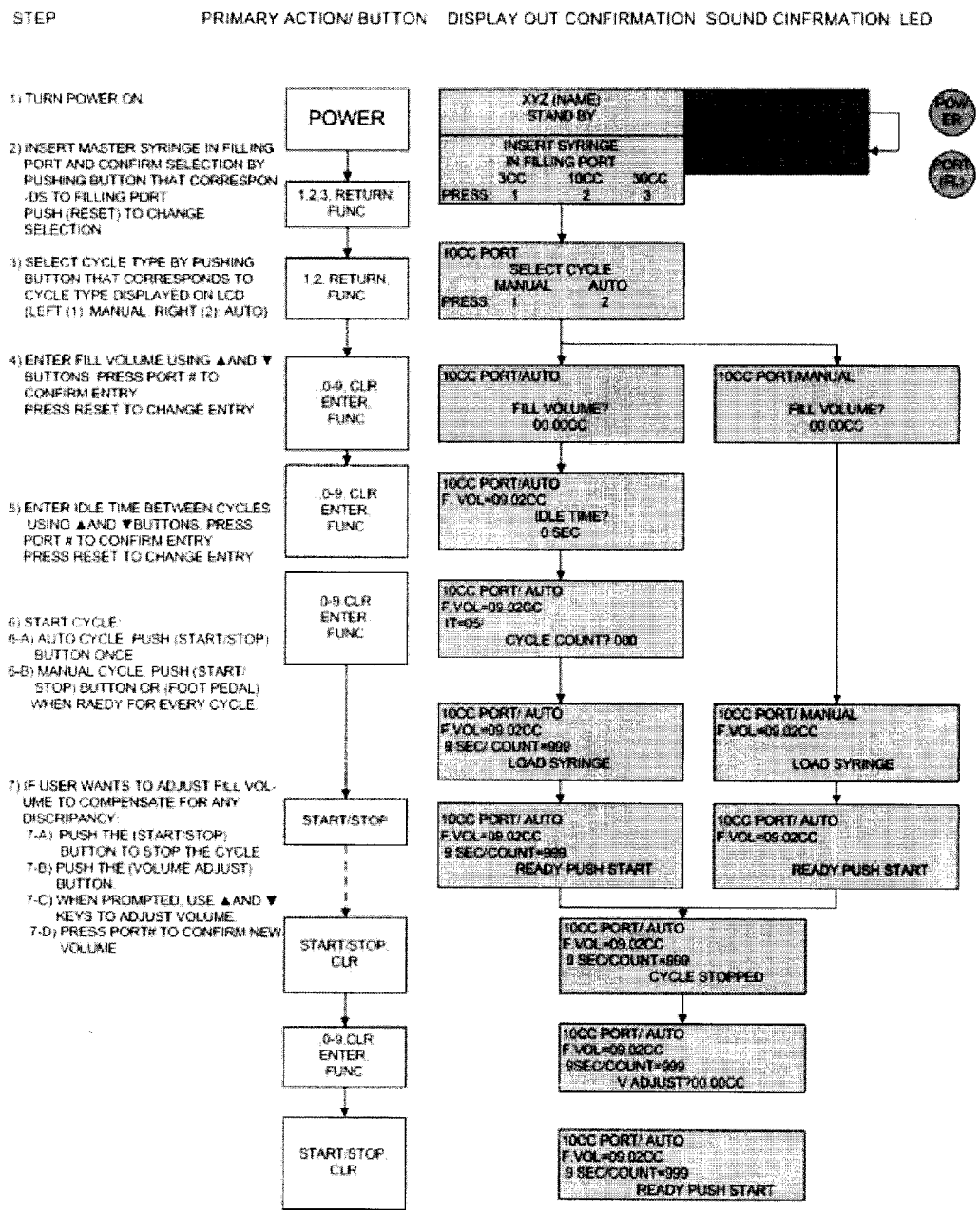
FIG. 5 is a flow chart of a method for filling containers such as syringes, bags, cassettes, etc., using the filling apparatus of FIG. 1.

Referring now to FIG. 5, the operations of the apparatus 10 will be described in more details.

At step 1, the operator powers up the apparatus 10. During the powering up, the apparatus 10 will initialize itself. During initialization, the controller 58 may instruct the step motor 54 to return to its default starting position.

At step 2, the operator can typically choose from recalling a previous filling setup, programming a new filling setup, or manual filling. The operator then selects the desired capacity (e.g. 3 cc, 10 cc or 30 cc) of the pumping syringe 12. Understandably, at this stage, a new pumping syringe 12 of the selected capacity should be properly installed in the channel 16 corresponding to its size, with the thumb rest of the plunger 14 being inserted in the proper groove 42.

At step 3, the operator selects the mode of operation. In the present apparatus 10, there are two operating modes, namely a manual mode and an automatic mode. The main differences between the manual mode and the automatic mode will be explained at step 6.

At step 4, the operator enters the desired filling volume using either the number button or the up-and-down arrow buttons. The operator could also select pre-programmed filling volumes if such pre-programmed filling volumes are available.

The operator also enters the speed at which the filling is performed to take into account the viscosity of the liquid drug to be transferred. It is to be understood that some drugs are more viscous than others and that the filling speed can affect the precision of the filling depending on the viscosity of the drugs. In the present embodiment, there are three speeds, namely low, medium and high, for each intermediate syringe size. For instance, for a 3 cc syringe, the low, medium and high speeds are respectively 0.261 cc/sec, 0.72 cc/sec and 1.62 cc/sec, for a 10 cc syringe, the low, medium and high speeds are respectively 0.40 cc/sec, 1.12 cc/sec and 2.52 cc/sec, and for a 30 cc syringe, the low, medium and high speeds are respectively 0.64 cc/sec, 1.75 cc/sec and 3.96 cc/sec. Linearly, the low, medium and high speeds are respectively 4.5 mm/sec, 7 mm/sec and 11 mm/sec. The low, medium and high speeds respectively correspond to three levels of viscosity, namely high, medium and low. In other words, the higher the viscosity, the lower the speed. It is important to understand that the filling speed should be chosen properly in order to avoid and preferably eliminate any turbulent flow during the filing procedure. In that sense, different types of high pressure tubing 24 could be used depending on the viscosity of the liquid.

At step 5, which is required only in automatic mode, once the desired filling volume is confirmed, the operator enters next the idle time, typically in seconds, either via the number button or via the up-and-down arrow buttons. The idle time is the time during which the apparatus 10 remains idle when one receiving syringe has been filled. The idle time allows the operator to remove the filled receiving syringe and to install a new and empty receiving syringe. Depending on the level of manipulation required once a receiving syringe is filled, the idle time may be more or less long.

At step 6, the operator confirms that the filling procedure can begin.

If it is a first filling of a new batch, the operator may need to prime the tubing 24 by eliminating air inside the tubing 24.

If the apparatus 10 is in manual mode, than the operator needs to manually start the filling for each receiving syringe, typically by pressing on the start button of the keyboard 36. A pedal, not shown, connected to the controller 58, could also be used to initiate the filling.

If the apparatus 10 is in automatic mode, than the operator only needs to start the filling of the first receiving syringe, via the start button, and the apparatus 10 will fill receiving syringes until the operator presses on the stop button of the keyboard 36 or until a pre-programmed number of syringes is reached. Understandably, in the automatic mode, the idle time is used to remove a pre-filled receiving syringe from the receiving station 26 and to replace it with an empty receiving syringe on the receiving station 26. The idle time should therefore be appropriately selected to provide enough time for the removal and installation of receiving syringes while avoiding spillage.

At step 6, during the filling of each receiving syringe, the controller 58 controls the step motor 54 to first pump the liquid drug from the bulk source into the pumping syringe 12, and then to pump the drug out of the pumping syringe 12 and into the receiving syringe via the dual check valve 22 and the high pressure tubing 24. This pumping cycle is repeated for each receiving syringe.

Still, if the receiving syringe, or the receiving container, has a capacity which is greater than the capacity of the pumping syringe 12, then the filling of the receiving syringe could require several pumping cycles.

As a guide, in the present embodiment, when the amount to be packaged in the receiving syringe (or container) is between 0.1 mL and 2.7 mL, the pumping syringe 12 is typically a 3 cc syringe. When the amount to be packaged in the receiving syringe (or container) is between 2.7 mL and 9.5 mL, the pumping syringe 12 is typically a 10 cc syringe. Finally, when the amount to be packaged in the receiving syringe (or container) is between 9.5 mL and 999 mL, the pumping syringe 12 is typically a 30 cc syringe.

At step 7, if the amount of drug in the receiving syringes is not as required, the operator can adjust the volume of drug by stopping the filling procedure by pressing the adjust button, and then enter the filled volume of drug. The controller 58 will then do the necessary calculation and correction. This manual adjustment can occur when, for instance, there are some discrepancies between the entered volume of drug and the volume of drug effectively transferred into the receiving syringes. The calibrating procedure about to be described should however limit the need for manual adjustments.

In the present embodiment, the calibrating procedure is performed as follows. First, the linear displacement $L_{SM}$ of a step of the step motor 54 must be determined. Typically, this value of $L_{SM}$ is known from the manufacturer of the step motor 54. In the present case, based on the model of step motor 54 mentioned above, the step equals to 0.024384 mm (for a rotation of) 1.8°. Then, for each pumping syringe 12 size, the volume $V_{SM}$ corresponding to the linear displacement $L_{SM}$ of a step of the step motor 54 must also be determined. This value of $V_{SM}$ can easily be obtained by multiplying $L_{SM}$ by the area $A_S$ of the interior of the barrel 13 of the pumping syringe 12. Then, for a particular desired volume $V_D$, the number of steps required to be performed by the step motor 54 to move the plunger to the correct position is calculated by dividing the desired volume $V_D$ by the volume $V_{SM}$ of a step of the step motor 54. These calculations are typically performed by the controller 58 of the apparatus 10.

However, as the area $A_S$ of the barrel 13 of the pumping syringe 12 can slightly vary from one pumping syringe 12 to another, there may be a slight discrepancy between the desired volume $V_D$ and the volume effectively transferred $V_E$.

Hence, during the calibrating procedure, the controller 58 of the apparatus 10 will calculate the required number of steps $N_{SM}$ in order to obtain the desired volume $V_D$. The operator will then start the apparatus 10 to transfer the liquid according to the calculated number of steps $N_{SM}$.

The operator will then enter the volume effectively transferred $V_E$ and the controller 58 will determine the error $E_V$ and make the necessary corrections.

The operator will then enter the error $E_V$ and the controller 58 will calculate the number of steps to either add or subtract from the calculated number of steps in order to compensate for the error.

The operator will then start the apparatus 10 again to transfer liquid according to the corrected number of steps.

The operator will then compare the new volume effectively transferred $V_E$ with the desired volume $V_D$ in order to determine the new error.

The calibrating procedure is reiterated until the volume effectively transferred $V_E$ in the receiving syringe corresponds to the desired volume $V_D$, taking into account acceptable margin of error. The margin of error is typically necessary because there is variation among syringes, typically in the order of 3%, and there is also an error of up to 5% caused by the resistance of plastic syringes which is not totally accurate.

When the volume effectively transferred $V_E$ is equal to the desired volume $V_D$, the calibrating procedure is completed. The correct number of steps of the step motor 54 will then be stored into the memory of the controller 58 for immediate and/or future use.

Understandably, depending on the required precision of the volume of liquid drug effectively transferred into the receiving syringe (or container), the calibrating procedure can be performed each time a new pumping syringe 12 is used (for more precise results) or can be performed once for a particular type of pumping syringe 12 (for less precise results). Still, it remains that the calibrating procedure should be performed as often as required by the degree of precision needed.

Typically, the calibrating procedure must be repeated for every new drug, even if the desired amount is the same, since the viscosity of the drug can affect the precision of the filling.

Understandably, though the present embodiment has been described in relation to receiving syringe, other receiving containers could be used.

In addition, in consideration for the need in a health care environment to ensure that the overall operation, together with the resulting filled receiving syringe, remain sterile, the apparatus 10 could be used under a hood to prevent contamination.

While illustrative and presently preferred embodiments of the invention have been described in detail hereinabove, it is to be understood that the inventive concepts may be otherwise variously embodied and employed and that the appended claims are intended to be construed to include such variations except insofar as limited by the prior art.

The invention claimed is:

1. A filling apparatus for filling a container with a liquid, the apparatus comprising:
    a housing supported by a base structure, the base structure comprising a supporting structure configured to releasably support at least one barrel of at least one pumping syringe, the supported structure comprising at least one channel formed into the housing and configured to releasably support the at least one barrel of the at least one pumping syringe;
    an actuating member slidingly mounted to the base structure, the actuating member being configured to releasably engage at least one plunger of the at least one pumping syringe;
    a linear actuator fixedly mounted to the base structure and drivingly connected to the actuating member for linearly displacing the actuating member, wherein the linear actuator member comprises a step motor driving a thread shaft drivingly engaged to the actuating member such that rotation of the threaded shaft causes the actuating member to slide; and
    a controller operatively connected to the linear actuator for controlling the linear actuator according to a predetermined program;
    wherein the step motor, the linear actuator and the actuating member are protected by the housing and remain accessible via at least one door providing access to the at least one channel and to the actuating member such as to protect the at least one channel and the actuating member from contaminants; wherein the at least one door is operatively connected to the controller such that opening the at least one door during will cause the apparatus to stop completely.

2. The filling apparatus as claimed in claim 1, further comprising a receiving structure mounted to the base structure and configured to releasably support connecting tubing.

3. The filling apparatus as claimed in claim 2, wherein the connecting tubing further comprises a dual check valve configured to be fluidly connected to the at least one pumping syringe, and a container connector configured to be fluidly connected to the container.

4. The filling apparatus as claimed in claim 3, wherein the housing comprises a control panel in communication with the controller.

5. The filling apparatus as claimed in claim 3, wherein the actuating member comprises at least one groove to releasably engage at least one free extremity of the at least one plunger of the at least one pumping syringe.

6. The filling apparatus as claimed in any claim 1, wherein the actuating member comprises at least one groove to releasably engage at least one free extremity of the at least one plunger of the at least one pumping syringe.

7. The filling apparatus as claimed in claim 1, wherein the base structure comprises a sliding structure configured to slidingly support the actuating member.

8. The filling apparatus as claimed in claim 7, wherein the sliding structure comprises at least one rod extending between a pair of supporting walls.

9. The filling apparatus as claimed in claim 8, wherein the linear actuator is mounted to one of the supporting walls.

10. The filling apparatus as claimed in claim 9, wherein the sliding structure comprises two rods extending between the pair of supporting walls.

11. The filling apparatus as claimed in claim 8, wherein the sliding structure comprises two rods extending between the pair of supporting walls.

12. The filling apparatus as claimed in claim 1, wherein the housing comprises a control panel in communication with the controller.

13. The filling apparatus as claimed in claim 1, wherein the at least one doors comprises two overlapping first and second doors with the second door overlapping the first door and generally covering an upper half portion of the at least one pumping syringe, including the at least one plunger, such that accidents are prevented and that the plunger remains protected from contaminants.

14. The filling apparatus as claimed in claim 13, wherein the second door is hingedly mounted to the housing, the first door being located under the second door and generally covers the linear actuator, the first door being also hingely mounted to the housing.

15. The filling apparatus as claimed in claim 1, wherein the step motor is configured to rotate by increment of 1.8 degree, which corresponds to a linear displacement of 0.024834 mm per step.

16. A filling apparatus for filling a syringe with a liquid, the apparatus comprising:
a base structure comprising a housing, the housing comprising at least one channel configured to releasably support at least one barrel of at least one pumping syringe;
an actuating member slidingly mounted to the base structure and within the housing, the actuating member being configured to releasably engage at least one plunger of the at least one pumping syringe;
a linear actuator mounted to the base structure and within the housing, the linear actuator being drivingly connected to the actuating member for linearly displacing the actuating member, wherein the linear actuator comprises a step motor driving a threaded shaft drivingly engaged to the actuating member such that rotation of the threaded shaft causes the actuating member to slide; and
a programmable controller operatively connected to the linear actuator for controlling the linear actuator according to a predetermined program;
wherein the housing comprises at least one door providing access to the at least one channel and to the actuating member such as to protect the at least one channel and the actuating member from contaminants, the at least one door being operatively connected to the programmable controller such that opening the at least one door causes the apparatus to stop completely.

17. The filling apparatus as claimed in claim 16, further comprising a receiving structure mounted to the base structure and configured to support connecting tubing.

18. The filling apparatus as claimed in claim 17, wherein the connecting tubing further comprises a dual check valve configured to be fluidly connected to the at least one pumping syringe, and a syringe connector configured to be fluidly connected to the syringe.

19. The filling apparatus as claimed in claim 18, wherein the housing comprises a control panel in communication with the controller.

20. The filling apparatus as claimed in claim 18, wherein the actuating member comprises at least one groove to releasably engage at least one free extremity of the at least one plunger of the at least one pumping syringe.

21. The filling apparatus as claimed in claim 16, wherein the actuating member comprises at least one groove to releasably engage at least one free extremity of the at least one plunger of the at least one pumping syringe.

22. The filling apparatus as claimed in claim 16, wherein the base structure comprises a sliding structure configured to slidingly support the actuating member.

23. The filling apparatus as claimed in claim 22, wherein the sliding structure comprises at least one rod extending between a pair of supporting walls.

24. The filling apparatus as claimed in claim 23, wherein the linear actuator is mounted to one of the pair of supporting walls.

25. The filling apparatus as claimed in claim 24, wherein the sliding structure comprises two rods extending between the pair of supporting walls.

26. The filling apparatus as claimed in claim 23, wherein the sliding structure comprises two rods extending between the pair of supporting walls.

27. The filling apparatus as claimed in claim 16, wherein the housing comprises a control panel in communication with the controller.

28. The filling apparatus as claimed in claim 16, wherein the least one doors comprises two overlapping first and second doors with the second door overlapping the first door, and generally covering an upper half portion of the at least one pumping syringe, including the at least one plunger, such that accidents are prevented and that the plunger remains protected from contaminants.

29. The filling apparatus as claimed in claim 28, wherein the second door is hingedly mounted to the housing, the first door being located under the second door and generally covers the threaded shaft and the step motor, the first door being also hingely mounted to the housing.

30. The filling apparatus as claimed in claim 16, wherein the step motor is configured to rotate by increment of 1.8 degree, which corresponds to a linear displacement of 0.024834 mm per step.

* * * * *